United States Patent [19]
Cole

[11] Patent Number: 5,866,766
[45] Date of Patent: Feb. 2, 1999

[54] INBRED SUNFLOWER LINE PHA262

[75] Inventor: Glenn S. Cole, Woodland, Calif.

[73] Assignee: Pioneer Hi-Bred International, Inc., Des Moines, Iowa

[21] Appl. No.: 783,916

[22] Filed: Jan. 17, 1997

[51] Int. Cl.⁶ .............................. A01H 1/02; A01H 5/10; A01H 1/00; C12N 5/04
[52] U.S. Cl. .................. 800/200; 800/255; 800/DIG. 14; 47/58; 47/DIG. 1; 435/412; 435/424; 435/430; 435/430.1
[58] Field of Search ...................................... 800/200, 255, 800/205, DIG. 14, 69, 250; 47/58, DIG. 1; 435/412, 424, 430, 430.1; 554/224

[56] References Cited

U.S. PATENT DOCUMENTS 5,461,171  10/1995  Heaton et al. ......................... 554/224

OTHER PUBLICATIONS

Phillips et al. Cell/Tissue Culture and In vitro Manipulation. ASA Pub #18, pp. 358, 1988.

Report No. 16, Manitoba Regional Sunflower Performance Tests–1995, Sponsored by the Manitoba Sunflower Committee (Jan. 2, 1996).

*Primary Examiner*—Gary Benzion
*Attorney, Agent, or Firm*—Pioneer Hi-Bred International, Inc.

[57] ABSTRACT

An inbred sunflower line, designated PHA262, the plants and seeds of inbred sunflower line PHA262, methods for producing a sunflower plant produced by crossing the inbred line PHA262 with itself or with another sunflower plant, and hybrid sunflower seeds and plants produced by crossing the inbred line PHA262 with another sunflower line or plant.

10 Claims, No Drawings

INBRED SUNFLOWER LINE PHA262

FIELD OF THE INVENTION

This invention is in the field of sunflower breeding, specifically relating to an inbred sunflower line designated PHA262.

BACKGROUND OF THE INVENTION

The goal of plant breeding is to combine in a single variety or hybrid various desirable traits. Major objectives in sunflower breeding include improved seed yield, earlier maturity, shorter plant height, uniformity of plant type, and disease and insect resistance. High oil percentage is important in breeding oilseed types whereas large seed size, a high kernel-to-hull ratio, and uniformity in seed size, shape, and color are important objectives in breeding and selection of nonoilseed sunflower. Other characteristics such as improved oil quality, protein percentage and protein quality are also important breeding objectives.

Sunflower are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

Sunflower (*Helianthus annuus* L.), can be bred by both self-pollination and cross-pollination techniques. The sunflower head (inflorescence) usually is composed of about 1,000 to 2,000 individual disk flowers joined to a common base (receptacle). The flowers around the circumference are ligulate ray flowers with neither stamens nor pistil. The remaining flowers are hermaphroditic and protandrous disk flowers.

Natural pollination of sunflower occurs when flowering starts with the appearance of a tube partly exserted from the sympetalous corolla. The tube is formed by the five syngenesious anthers, and pollen is released on the inner surface of the tube. The style lengthens rapidly and forces the stigma through the tube. The two lobes of the stigma open outward and are receptive to pollen but out of reach of their own pollen initially. Although this largely prevents self-pollination of individual flowers, flowers are exposed to pollen from other flowers on the same head by insects, wind, and gravity.

A reliable method of controlling male fertility in plants offers the opportunity for improved plant breeding. This is especially true for development of sunflower hybrids, which relies upon some sort of male sterility system. Two types of male sterility, genetic and cytoplasmic, have been found in sunflower.

Hybrid sunflower seed is typically produced by a male sterility system incorporating genetic or cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in sunflower plants, since only the female provides cytoplasm to the fertilized seed. CMS plants are fertilized with pollen from another inbred that is not male-sterile. Pollen from the second inbred may or may not contribute genes that make the hybrid plants male-fertile.

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. These and all patents referred to are incorporated by reference. In addition to these methods, Albertsen et al., of Pioneer Hi-Bred, U.S. patent application Ser. No. 07/848,433, have developed a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

There are many other methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see: Fabinjanski, et al. EPO 89/3010153.8 publication no. 329, 308 and PCT application PCT/CA90/00037 published as WO 90/08828).

The use of male sterile inbreds is but one factor in the production of sunflower hybrids. The development of sunflower hybrids requires, in general, the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other broad-based sources into breeding pools from which new inbred lines are developed by selfing and selection of desired phenotypes. The new inbreds are crossed with other inbred lines and the hybrids from these crosses are evaluated to determine which of those have commercial potential.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \rightarrow F_2$; $F_3 \rightarrow F_4$; $F_4 \rightarrow F_5$, etc.

A single cross hybrid sunflower variety is the cross of two inbred lines, each of which has a genotype that complements the genotype of the other. The hybrid progeny of the first generation is designated $F_1$. In the development of hybrids only the $F_1$ hybrid plants are sought. Preferred $F_1$ hybrids are more vigorous than their inbred parents. This hybrid vigor, or heterosis, can be manifested in many polygenic traits, including increased vegetative growth and increased yield.

The development of a hybrid sunflower variety involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrid progeny ($F_1$). During the inbreeding process in sunflower, the vigor of the lines decreases. Vigor is restored when two different inbred lines are crossed to produce the hybrid progeny ($F_1$). An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

A single cross hybrid is produced when two inbred lines are crossed to produce the $F_1$ progeny. A double cross hybrid is produced from four inbred lines crossed in pairs (A×B and C×D) and then the two $F_1$ hybrids are crossed again (A×B)× (C×D). Much of the hybrid vigor exhibited by $F_1$ hybrids is lost in the next generation ($F_2$). Consequently, seed from hybrid varieties is not used for planting stock.

Sunflower is an important and valuable field crop. Thus, a continuing goal of plant breeders is to develop high-yielding sunflower hybrids that are agronomically sound based on stable inbred lines. The reasons for this goal are obvious: to maximize the amount of seed produced with the inputs used and minimize susceptibility of the crop to environmental stresses. To accomplish this goal, the sunflower breeder must select and develop superior inbred parental lines for producing hybrids. This requires identification and selection of genetically unique individuals that occur in a segregating population. The segregating population is the result of a combination of crossover events plus the independent assortment of specific combinations of alleles at many gene loci that results in specific genotypes. Based on the number of segregating genes, the frequency of occurrence of an individual with a specific genotype is less than 1 in 10,000. Thus, even if the entire genotype of the parents has been characterized and the desired genotype is known, only a few if any individuals having the desired genotype may be found in a large $F_2$ or $S_0$ population. Typically, however, the genotype of neither the parents nor the desired genotype is known in any detail.

In addition to the preceding problem, it is not known how the genotype will react with the environment. This genotype by environment interaction is an important, yet unpredictable, factor in plant breeding. A breeder of ordinary skill in the art cannot predict the genotype, how that genotype will interact with various environments or the resulting phenotypes of the developing lines, except perhaps in a very broad and general fashion. A breeder of ordinary skill in the art would also be unable to recreate the same line twice from the very same original parents as the breeder is unable to direct how the genomes combine or how they will interact with the environmental conditions. This unpredictability results in the expenditure of large amounts of research resources in the development of a superior new sunflower inbred line.

Pioneer research station staff propose about 400 to 500 new inbreds each year from over 2,000,000 pollinations. Of those proposed new inbreds, less than 50 and more commonly less than 30 are actually selected for commercial use.

SUMMARY OF THE INVENTION

According to the invention, there is provided a novel inbred sunflower line, designated PHA262. This invention thus relates to the seeds of inbred sunflower line PHA262, to the plants of inbred sunflower line PHA262, and to methods for producing a sunflower plant produced by crossing the inbred line PHA262 with itself or another sunflower line. This invention further relates to hybrid sunflower seeds and plants produced by crossing the inbred line PHA262 with another sunflower line.

DEFINITIONS

In the description and examples that follow, a number of terms are used herein. In order to provide a clear and consistent understanding of the specification and claims, including the scope to be given such terms, the following definitions are provided. NOTE: ABS is in absolute terms and %MN is percent of the mean for the experiments in which the inbred or hybrid was grown. These designators will follow the descriptors to denote how the values are to be interpreted. Below are the descriptors used in the data tables included herein.

$/ACR=A calculated trait of the value of oil obtained. Yield (LBS/10) multiplied by the percent oil (OIL10P) multiplied by the average cost paid for sunflower.

50PFLW—The number of days it takes for 50 percent of the plants to reach the stage of R5.1 R5.1 is when the ray flowers are visible and the first ring of disk flowers has emerged and flowered.

BNKSC—A 1 to 9 visual rating indicating the level of neck breakage. The higher the score the less breakage that occurs.

BSKSC—A 1 to 9 visual rating indicating the level of stalk breakage. The higher the score the less breakage that occurs.

CLD TST=COLD TEST. The percent of plants that germinate under cold test conditions.

CTRSET=A 1 to 9 visual rating indicating the degree of seed set obtained within the sunflower head. A 1 equals a head where only the outer 10% of the head sets seed. A 9 equals a head where 90–100% of the head sets seed.

CYTOPLASMIC MALE STERILE (CMS) PLANT OR INBRED LINE. A sunflower line that produces no viable pollen is called male sterile. Male sterility is inherited maternally, i.e. the male sterile plant is used as the female parent in a cross with pollen from another sunflower. CMS lines are produced by crossing a maintainer line with a sunflower plant with the cytoplasmic male sterility trait and then backcrossing to the maintainer line until a male sterile line that is homologous to the maintainer line in all other respects is developed. CMS lines are also referred to as female lines.

D/D=DRYDOWN. This represents the relative rate at which a hybrid will reach acceptable harvest moisture compared to other hybrids on a 1–9 rating scale. A high score indicates a hybrid that dries relatively fast while a low score indicates a hybrid that dries slowly.

DNYMLW=A 1 to 9 visual rating indicating the resistance to Downy Mildew (*Plasmopara halstedii*). A higher score indicates greater resistance.

DYSR9=The number of days it takes for 50 percent of the plants to reach the R9 flowering stage. This is a stage of physiological maturity that is determined when the back of the flowering head has reached a yellowing stage and the outer bracts of the head have started to brown. This normally is a stage when the seed moisture is at about 30–40% moisture.

HARHT=This is the height of the head at harvest, measured in decimeters.

HARMST=This is a measure of seed moisture taken at harvest time. It is recorded in percentage of moisture to seed weight.

LBS/10=The grain yield as measured in pounds divided by 10.

OIL10P=The percentage of oil content measured from the harvested grain adjusted to a 10% moisture level.

PHOSC=A 1 to 9 visual rating indicating the resistance to Phompsis stalk rot (Phompsis helianthii). A higher score indicates a greater resistance.

PLTHT=This is the height of the head at flowering, measured in decimeters.

PMASC=A 1 to 9 visual rating indicating the resistance to Phoma stalk rot (Phoma macdonaldii. The higher score indicates a greater resistance.

R160=A measure of the percentage of Palmitic acid found in the oil of the seed as measured by a rapid reading from a gas chromatograph.

R180=A measure of the percentage of Stearic acid found in the oil of the seed as measured by a rapid reading from a gas chromatograph.

R181=A measure of the percentage of Oleic acid found in the oil of the seed as measured by a rapid reading from a gas chromatograph.

R182=A measure of the percentage of Linoleic acid found in the oil of the seed as measured by a rapid reading from a gas chromatograph.

RESTORER LINE. A line possessing the gene or genes to restore male fertility or viable pollen to a sunflower hybrid or inbred line and progeny having a maternal cytoplasm that conditions male sterility. This term is also discussed in the literature. See for e.g. Fick, "Breeding and Genetics," in Sunflower Science and Technology 279–388 (J. F. Carter ed. 1978), the contents of which are incorporated herein by reference.

RLGSC=A 1 to 9 visual rating indicating the level of root lodging. The higher the score the less root lodging that occurs.

RSTSC=A 1 to 9 visual rating indicating the resistance to Rust (Puccinia helianthii). A higher score indicates greater resistance.

SCLHSC=A 1 to 9 visual rating indicating the resistance to Sclerotinia (Sclerotinia sclerotiorum), head infection. A higher score indicates a greater resistance.

SCLRSC=A 1 to 9 visual rating indicating the resistance to Sclerotinia (Sclerotinia sclerotiorum), root and basal stalk infection. A higher score indicates a greater resistance.

SLFFER=A 1 to 9 visual rating indicating the detree of self fertility found within a self pollinated head. A score of 1 indicates <10% of the seed sets under a bagged self. A score of 9 indicates that 90–100% of the seed sets under a bagged self.

STA GRN=STAY GREEN. Stay green is the measure of plant health near the time of black layer formation (physiological maturity). A high score indicates better late-season plant health.

STMCRV=A 1 to 9 visual rating indicating the degree of stem curvature and head ttitude. A 1 indicates a very pendulous neck and head whereas a 9 indicates virtually no neck bend and an erect head attitude.

SUNFLOWER SEED. Botanically referred to as an "achene", comprised of the pericarp and embryo.

VERWLT=A 1 to 9 visual rating indicating the resistance to Verticillium wilt (Verticillium dahliae). A higher score indicates a greater resistance.

DETAILED DESCRIPTION OF THE INVENTION

Inbred sunflower lines are typically developed for use in the production of hybrid sunflower lines. Inbred sunflower lines need to be highly homogeneous, homozygous and reproducible to be useful as parents of commercial hybrids. There are many analytical methods available to determine the homozygotic and phenotypic stability of these inbred lines.

The oldest and most traditional method of analysis is the observation of phenotypic traits. The data is usually collected in field experiments over the life of the sunflower plants to be examined. Phenotypic characteristics most often observed are for traits associated with plant morphology, flower morphology, insect and disease resistance, maturity, and yield.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites.

Inbred sunflower line PHA262 is a high oleic, sunflower inbred that is best suited as a female in crosses for producing first generation F1 sunflower hybrids. PHA262 is best adapted to sunflower growing regions of the northern plains of the United States, Canada, and France. PHA262 yields competitively with top conventional oil hybrids and has better stalk quality. The inbred plant characteristics include high oleic conent.

The inbred has shown uniformity and stability within the limits of environmental influence for all the traits as described in the Variety Description Information (Table 1) that follows. The inbred has been self-pollinated a sufficient number of generations with careful attention paid to uniformity of plant type to ensure the homozygosity and phenotypic stability necessary to use in commercial production. The line has been increased both by hand and in isolated fields with continued observation for uniformity. No variant traits have been observed or are expected in PHA262.

Inbred sunflower line PHA262, being substantially homozygous, can be reproduced by planting seeds of the line, growing the resulting sunflower plants under self-pollinating or sib-pollinating conditions with adequate isolation, and harvesting the resulting seed, using techniques familiar to the agricultural arts.

TABLE 1

VARIETY DESCRIPTION INFORMATION
INBRED = PHA262

| | |
|---|---|
| Class: Oil Type | Region Best Adapted: Sunflower growing regions of the U.S.A., Canada, northern and western Europe |
| A. Maturity: | |
| Head First Visible (from emergence): | 64 |
| Harvest Ripeness: | 95 |
| B. Plant Characteristics: | |
| Plant height: | 105 cm |
| C. Stem: | |
| Length of Internode at Harvest Ripeness: | 3.8 |
| Number of Leaves: | 28 |
| Branching: | No Branching |
| Color of Growing Point: | Green |
| D. Leaves: | |
| Blade Length: | 28.0 cm |
| Blade Width: | 25.0 cm |
| Width:Length Ratio: | Narrower Than Long |
| Leaf Shape: | Cordate |
| Leaf Apex: | Acuminate |
| Leaf Base: | Auriculate |
| Leaf Margin: | Coarsely Crenate |
| Depth of Margin Indentation: | Intermediate |
| Attitude: | Descending |
| Surface: | Crinkled (ridged) |
| Color: | Green |
| Margin Color: | Green |
| E. Head at Flowering: | |
| Ray Flowers: | Present |
| Ray Flower Color: | Yellow |
| Disk Flower Color: | Yellow |
| Anthocyanin in Stigmans: | Absent |
| Pollen Color: | Yellow |
| Pappi: | Green |
| Ray Length: | 63.0 mm |
| Ray Width: | 19.0 mm |
| F. Head at Seed Maturity: | |
| Diameter: | 16.0 cm |
| Receptacle Shape: | Convex |
| Head Attitute: | Slightly Descending |
| Seeds Per Head | 800 |
| G. Seeds: | |
| Outer Pericarp: | Striped Black |
| Middle Pericarp: | White |
| Inner Pericarp (seed coat): | No Color |
| Stripes: | Black With Narrow Dark-Grey Striping |
| Mottling: | Absent |
| Shape: | Narrowly Obovate |
| Shape (cross section) | Curved |
| Length | 14.0 mm |
| 100 seed | 6.0 gm |
| % Held on 7.9 mm (20/64) Round-Hole Screen | 0.0 |
| H. Diseases: | |
| Rust: | Not Tested |
| Verticillium Wilt (*V. Dahliae*): | Not Tested |
| Downy Mildew (*P. Halstedii*): | Not Tested |
| White Blister Rust (*A. Tragopogi*): | Not Tested |
| Broom Rape (*O. Cumanii*): | Not Tested |
| Sclerotinia Wilt (*S. Sclerotiorum*): | Not Tested |
| Leaf Mottle (*V. Albo-Atrum*): | Not Tested |
| Gray-Mold Blight, Bud Rot (*B. Cinerea*): | Not Tested |
| Charcoal Rot, Stem Rot (*M. Phaseolina*): | Not Tested |
| I. Isects: | |
| European Sunflower Moth (*H. Nebullela*): | Not Tested |
| Sunflower Moth (*H. Electellum*): | Not Tested |

*In interpreting the foregoing color designations, reference may be had to the Munsell Glossy Book of Color, a standard color reference.
All data collected from plots in Woodland, California in 1995.
(PVP Certificate No.) is a Pioneer Hi-Bred International, Inc. proprietary inbred.

INDUSTRIAL APPLICABILITY

This invention also is directed to methods for producing a sunflower plant by crossing a first parent sunflower plant with a second parent sunflower plant wherein the first or second parent sunflower plant is an inbred sunflower plant of the line PHA262. Further, both first and second parent sunflower plants can come from the inbred sunflower line PHA262. Thus, any such methods using the inbred sunflower line PHA262 are part of this invention: selfing, hybrid production, crosses to populations, and the like. All plants produced using inbred sunflower line PHA262 as a parent are within the scope of this invention. Advantageously, the inbred sunflower line is used in crosses with other, different, sunflower inbreds to produce first generation ($F_1$) sunflower hybrid seeds and plants with superior characteristics.

As used herein, the term plant includes plant cells, plant protoplasts, plant cell tissue cultures from which sunflower plants can be regenerated, plant calli, plant clumps, and plant cells that are intact in plants or parts of plants, such as embryos, pollen, ovules, flowers, leaves, husks, stalks, roots, root tips, anthers, and the like.

Several different methods are used to develop inbred lines depending on such factors as the source populations available and specific program objectives. The most common procedure involves selection of individual plants within open pollinated cultivars or segregating generations of planned crosses.

Although self pollination is used most commonly during the inbreeding process, sib pollinations also may have advantages in developing inbred lines. Aside from theoretical considerations involving the rate of approach to homozygosity, sib matings are especially useful when development or maintenance of lines with a high degree of self incompatability is desired.

In producing the inbred sunflower of the present invention, parent lines and varieties possessing desirable characteristics may be used to advantage. A preferred line can be obtained, following conventional sunflower breeding by self-pollination for a number if generations, usually three or more, of progeny or of crosses of Pervenets with other lines or varieties, selected for favorable characteristics. Similar breeding methods are described in Fernandez-Martinez, J., et al., Breeding for High Content of Oleic Acid in Sunflower (Helianthus annuus L.) Oil; Helia Nr. Scientific Bulletin of the F.A.O. Research Network on Sunflower 11–15 (1988); Fick, G. N., Sunflower, Oil Crops of the World Ch. 14 pp. 301–318 (1989); Knowles, P. F., Genetics and Breeding of Oil Crops, Oil Crops of the World Ch. 12 pp. 260–282 (1989).

After inbreeding has progressed to the point where progeny are true-breeding for a particular characteristic, the starting material is preferably converted to cytoplasmic male sterility (CMS), in accordance with the present invention, by crossing the selected Pervenets germplasm with a sunflower line, such as CMS HA89 (U.S. Department of Agriculture), that incorporates a cytoplasmic determinant for male sterility. The source of CMS HA89 and most other currently available CMS lines is from the material of Leclercq, "Cytoplasmic Sterility in the Sunflower," Ann. Amelior. Plant. (French) 19:99–106 (1969).

Inbred lines can also be developed through chromosome duplication of haploids. Author unknown. 1971. "Basic Principles of Sunflower Selection." pp. 417–465. Genectic Principles of Plant Selection. Nauka, Moscow. The main advantage of this method is that pure breeding lines may be developed without several years of inbreeding. The disadvantage is that haploids occur among twin seedlings at a frequency of only 0.64 to 4.76%. Thus, another aspect of this invention is to provide cells which upon growth and differentiation produce sunflower plants having the physiological and morphological characteristics of inbred line PHA262.

Duncan, Williams, Zehr, and Widholm, Planta, (1985) 165:322–332 reflects that 97% of the plants cultured which produced callus were capable of plant regeneration. Subsequent experiments with both inbred and hybrids produced 91% regenerable callus which produced plants. In a further study in 1988, Songstad, Duncan & Widholm in Plant Cell Reports (1988), 7:262–265 reports several media additions which enhance regenerability of callus of two inbred lines. Other published reports also indicated that "nontraditional" tissues are capable of producing somatic embryogenesis and plant regeneration. Thus, it is clear from the literature that the state of the art is such that these methods of obtaining plants are, and were, "conventional" in the sense that they are routinely used and have a very high rate of success. Thus, another aspect of this invention is to provide cells which upon growth and differentiation produce sunflower plants having the genotype of PHA262.

Sunflower (Helianthus annuus) oil is a major edible oil worldwide. The oil component of sunflower seeds typically contributes about 80 percent of the value of a sunflower crop and is mostly used as a cooking medium. Sunflower oil is also used as salad oil, as well as in the manufacture of margarine, soap, shortening, lubricants, and as a source for biodiesel fuels. In the United States, approximately 1–2 million acres are planted in sunflowers annually, primarily in the Dakotas and Minnesota.

The seed of inbred sunflower line PHA262, the plant produced from the inbred seed, the hybrid sunflower plant produced from the crossing of the inbred, hybrid seed, and various parts of the hybrid sunflower plant can be utilized for human food, livestock feed, and as a raw material in industry.

Performance Examples of PHA262

In the examples that follow, the traits and characteristics of inbred sunflower line PHA262 are given as a line. The data collected on inbred sunflower line PHA262 is presented for the key characteristics and traits.

The results in Table 2A compare Sunflower Hybrid PHA262 with a similarly adapted Pioneer Sunflower hybrid, PHA158. As can be seen from the results, PHA262 is higher yielding than PHA158.

The results in Table 2B compare Sunflower Hybrid PHA262 with a similarly adapted Pioneer Sunflower hybrid, PH043. As can be seen from the results, PHA262 is higher yielding than PH043.

TABLE 2A

VARIETY #1 PHA262
VARIETY #2 PHA158

|  | VAR # | QU/HA ABS | QU/HA % MN | SZD YLD ABS |
|---|---|---|---|---|
| TOTAL SUM | 1 | 19.1 | 89 | 16.4 |
|  | 2 | 21.5 | 100 | 13.9 |
|  | LOCS | 1 | 1 | 1 |
|  | REPS | 2 | 2 | 2 |
|  | DIFF PROB | 2.4 | 11 | 2.5 |
|  | VAR # | QU/HA ABS | QU/HA % MN | SZD YLD ABS |

* = 10% SIG
+ = 5% SIG
# = 1% SIG

TABLE 2B

VARIETY #1 - PHA262
VARIETY #2 - PHA043

|  | VAR # | QU/HA ABS | QU/HA % MN | SZD YLD ABS |
|---|---|---|---|---|
| TOTAL SUM | 1 | 19.1 | 89 | 16.4 |
|  | 2 | 16.4 | 77 | 14.4 |
|  | LOCS | 1 | 1 | 1 |
|  | REPS | 2 | 2 | 2 |
|  | DIFF PROB | 2.7 | 12 | 1.9 |
|  | VAR # | QU/HA ABS | QU/HA % MN | SZD YLD ABS |

* = 10% SIG
+ = 5% SIG
# = 1% SIG

Applicant has made a deposit of at least 2500 seeds of Inbred Sunflower Line PHA262 with the American Type Culture Collection (ATCC), Manassas, Va. 20110 USA, ATCC Deposit No. 203053. The seeds deposited with the ATCC on Jul. 10, 1998 were taken from the deposit maintained by Pioneer Hi-Bred International, Inc., 700 Capital Square, 400 Locust Street, Des Moines, Iowa 50309-2340 since prior to the filing date of this application. This deposit of the Inbred Sunflower Line PHA262 will be maintained in the ATCC depository, which is a public depository, for a period of 30 years, or 5 years after the most recent request, or for the effective life of the patent, whichever is longer, and will be replaced if it becomes nonviable during that period. Additionally, Applicant has satisfied all the requirements of 37 C.F.R. §§1.801–1.809, including providing an indication of the viability of the sample. Applicant imposes no restrictions on the availability of the deposited material from the ATCC; however, Applicant has no authority to waive any restrictions imposed by law on the transfer of biological material or its transportation in commerce. Applicant does not waive any infringement of its rights granted under this patent or under the Plant Variety Protection Act (7 USC 2321 et seq.). U.S. Plant Variety Protection of PHA262 has been applied for under Application No. 9700031.

The foregoing invention has been described in detail by way of illustration and example for purposes of clarity and understanding. However, it will be obvious that certain changes and modifications such as single gene modifications and mutations, somoclonal variants, variant individuals selected from large populations of the plants of the instant inbred and the like may be practiced within the scope of the invention, as limited only by the scope of the appended claims.

What is claimed is:

1. Seed of sunflower inbred line designated PHA262, representative seed of said inbred PHA262 having been deposited under Accession No. 203053.

2. A sunflower plant, or parts thereof, having all the physiological and morphological characteristics of inbred line PHA262, representative seed of said line having been deposited under ATCC accession No. 203053.

3. The sunflower plant of claim 2, wherein said plant is male sterile.

4. A tissue culture of regenerable cells of a sunflower plant of inbred line PHA262, wherein the tissue regenerates plants, such plants capable of expressing all the morphological and physiological characteristics of the inbred line PHA262, representative seed of which have been deposited under ATCC Accession No. 203053.

5. A tissue culture according to claim 4, the cells or protoplasts being from a tissue selected from the group consisting of leaves, pollen, embryos, roots, root tips, anthers, flowers and stalks.

6. A sunflower plant regenerated from the tissue culture of claim 4, capable of expressing all the morphological and physiological characteristics of inbred line PHA262, representative seed of which have been deposited under ATCC Accession No. 203053.

7. A method for producing a first generation ($F_1$) hybrid sunflower seed comprising crossing the plant of claim 2 with a different inbred parent sunflower plant and harvesting the resultant first generation ($F_1$) hybrid sunflower seed.

8. The method of claim 7 wherein inbred sunflower plant of claim 2 is the female or male parent.

9. An $F_1$ hybrid seed produced by crossing the inbred sunflower plant according to claim 2 with another, different sunflower plant.

10. An $F_1$ hybrid plant, or parts thereof, grown from the seed of claim 9.

* * * * *

UNITED STATES PATENT AND TRADEMARK OFFICE
CERTIFICATE OF CORRECTION

PATENT NO : 5,866,766

DATED : Feb. 2, 1999

INVENTOR(S): Glenn S. Cole

It is certified that error appears in the above-identified patent and that said Letters Patent is hereby corrected as shown below:

On the Title page of the patent, for the Appl. No., delete "783,916" and insert --08/783,916--.

In column 10, between Table 2B and line 19, insert the heading --Deposits--.

In column 10, line 21, delete "Va." and insert --VA--.

In column 10, line 23, delete "Jul." and insert --July--.

In column 10, between lines 49 and 50, insert the heading --Claims--.

Signed and Sealed this

Twenty-second Day of May, 2001

Attest:

NICHOLAS P. GODICI

Attesting Officer    Acting Director of the United States Patent and Trademark Office